United States Patent
Gill et al.

(10) Patent No.: US 7,792,572 B1
(45) Date of Patent: Sep. 7, 2010

(54) ISCHEMIA DETECTION USING INTRA-CARDIAC SIGNALS

(75) Inventors: Jong Gill, Valencia, CA (US); Peter Boileau, Valencia, CA (US); Gene A. Bornzin, Simi Valley, CA (US); Joseph J. Florio, La Canada, CA (US); Mohssen Fard, Woodland Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 1471 days.

(21) Appl. No.: 11/130,858

(22) Filed: May 16, 2005

Related U.S. Application Data

(60) Provisional application No. 60/572,312, filed on May 17, 2004.

(51) Int. Cl.
*A61B 5/0452* (2006.01)
(52) U.S. Cl. ............... 600/509; 600/508; 600/515; 600/516; 128/920
(58) Field of Classification Search ......... 600/508–509, 600/515–516; 128/920
See application file for complete search history.

(56) References Cited

U.S. PATENT DOCUMENTS

| | | | |
|---|---|---|---|
| 4,712,555 A | 12/1987 | Thornander et al. ... | 128/419 PG |
| 4,788,980 A | 12/1988 | Mann et al. ........... | 128/419 PG |
| 4,940,052 A | 7/1990 | Mann et al. ........... | 128/419 PG |
| 4,944,298 A | 7/1990 | Sholder ................ | 128/419 PG |
| 5,010,888 A * | 4/1991 | Jadvar et al. ................ | 600/509 |
| 5,466,254 A | 11/1995 | Helland ....................... | 607/123 |
| 5,476,483 A | 12/1995 | Bornzin et al. ................ | 607/17 |
| 6,314,323 B1 | 11/2001 | Ekwall ........................ | 607/23 |
| 6,377,852 B1 | 4/2002 | Bornzin et al. ................. | 607/9 |
| 6,865,420 B1 * | 3/2005 | Kroll ........................... | 607/25 |
| 2002/0138012 A1 * | 9/2002 | Hodges et al. .............. | 600/509 |
| 2003/0013978 A1 * | 1/2003 | Schlegel et al. ............. | 600/509 |

\* cited by examiner

*Primary Examiner*—Carl H Layno
*Assistant Examiner*—Deborah Malamud

(57) ABSTRACT

An implanted cardiac rhythm management device is disclosed that is operative to detect myocardial ischemia. This is done by evaluating electrogram features to detect an electrocardiographic change; specifically, changes in electrogram segment during the early part of an ST segment. The early part of the ST segment is chosen to avoid the T-wave.

16 Claims, 10 Drawing Sheets

ISCHEMIA DETECTION USING INTRA-CARDIAC SIGNALS

CROSS REFERENCE TO RELATED APPLICATIONS

This application claims the benefit of U.S. Provisional Application Ser. No. 60/572,312, filed May 17, 2004.

FIELD OF THE INVENTION

This invention relates to implanted medical devices and, more particularly, to implanted medical devices that are capable of detecting myocardial ischemia.

BACKGROUND

Myocardial ischemia results from insufficient blood flow to the heart muscle. Ischemia may occur chronically, and to varying degrees, due to coronary artery disease (CAD) or acutely due to sudden increased demand, embolism or vasospasm. Ischemia can lead to angina and eventually to myocardial infarction—permanent damage to the heart muscle. Moreover, both ischemia and infarction can trigger fatal arrhythmias.

Ischemia can be detected by electrocardiographic changes. Conventional detection is through ST segment elevation shown in surface ECG. Detection through surface ECG is done only briefly and infrequently in the clinic or through the use of a Holter monitor. Only those ischemic events which happen to occur, or which may be provoked by stress tests during monitoring are detected.

A long-term record of ischemia burden obtained through continuous monitoring would be very useful as an adjunct to current methods of ischemia detection and diagnosis. Such a record may reveal infrequent or unprovokable ischemia perhaps associated with nascent CAD, vasospasm or embolism. Such a record could reveal trends in the progression or regression of CAD. It could also be used to gauge the efficacy of, and/or patient compliance with, a course medication.

Implantable medical devices (IMDs), such as pacemakers and implantable cardiac defibrillators (ICDs), offer the ideal platform for ischemia burden monitoring. IMDs can constantly monitor the electrophysiological conditions of patients and detect the onset and/or the burden of ischemia. Prior patents such as U.S. Pat. No. 6,108,577 issued to Michael Benser or U.S. Pat. No. 6,609,023 issued to Fischell et al. describe the detection of ischemia based on ST level change detected from EGMs of implanted lead electrodes.

The capability to detect ischemia may have other applications in IMDs. Because myocardial perfusion occurs during diastole, lower heart rates are conducive to better perfusion. Therefore, an IMD should avoid pacing at high rates if ischemia is detected. An IMD may perhaps even force a ventricular rate lower than the sinus rate through special pacing techniques such as the one described in U.S. Pat. No. 6,377,852 by Bomzin et al. IMDs may also alert patients of silent (asymptomatic) ischemic events so that they may take appropriate action such as taking medication, ceasing exertion, lying down etc. IMDs may also release thrombolytic or antithrombotic medication upon the detection of ischemia.

SUMMARY

What is described herein is a method by which an implanted cardiac rhythm management device may detect myocardial ischemia. This is done by evaluating electrogram features to detect an electrocardiographic change; specifically, changes in electrogram segment between S and T waves, and specifically during the early part of a ST segment. In one embodiment, the early part of the ST segment can be the period approximately 50-100 milliseconds after onset of the Q-wave, or 100-150 milliseconds from onset of the Q-wave, or even between 150-200 milliseconds following the onset of the Q-wave.

Focusing on the early part of ST segment has an advantage in that the potential loss of ST segment specificity for ischemia detection due to T wave modulations is reduced. T-wave morphology may be affected by numerous metabolic, non-cardiac, and cardiac conditions other than ischemia.

Secondly, concentration on the early portion of the ST segment allows the ischemic detection to be performed independent of ST interval changes due to rate variations. In other words, the elimination of a need to determine the time at which a T wave occurs removes potential complicated methodologies that might be necessary due to wide variations of ST intervals due to varying heart rates.

In another embodiment, the ST segment measurements are made in reference to pre-P levels rather than a PQ interval value. It is observed that the baseline between P and Q wave can be modulated by ischemic conditions if the occlusion occurs at arteries supplying blood to the atria as well as ventricles. Therefore, in order to eliminate the possibility of the ST adjustment being affected by drift in PQ baseline, ST segment adjustment will be made in reference to the pre-P level.

DETAILED DESCRIPTION

The following description is not to be taken in a limiting sense, but rather is made merely for the purpose of describing the general principles of the illustrative embodiments. The scope of the invention should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to deliver cardiac therapy and/or sense information germane to cardiac performance and/or therapy.

Figure 1:
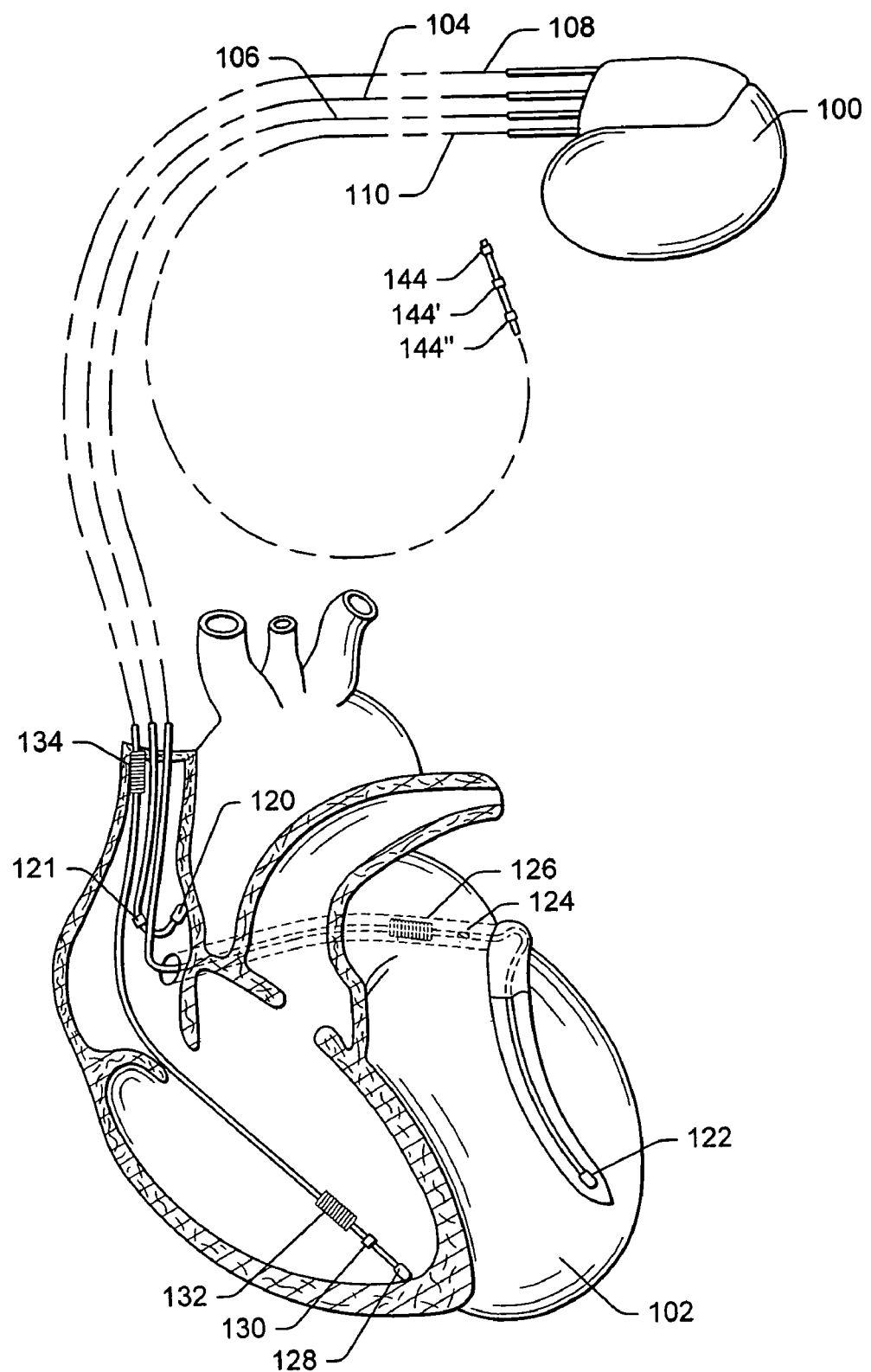
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary implantable medical device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to sense atrial and ventricular cardiac activity, and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
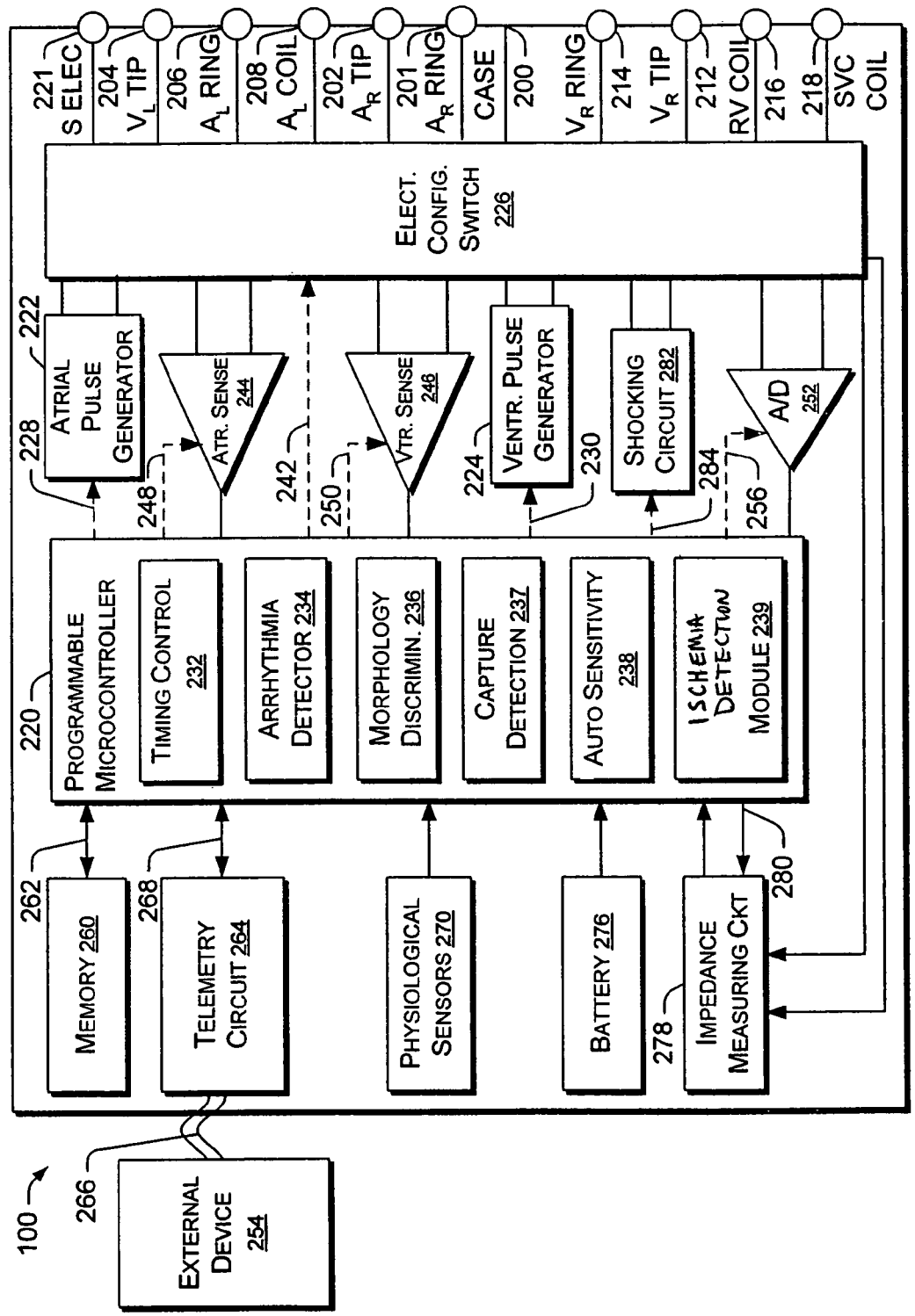
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac detection and/or therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237, an auto sensing module 238 and an ischemia detection module 239. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The ischemia detection module 239, as described in greater detail below, may aid in acquisition, analysis, etc., of information relating to ischemia detection.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. Such a module is optionally suitable for performing various exemplary methods described herein. For example, such a module (e.g., the module 234, the module 239, etc.) optionally allows for analyses related to action potentials (e.g., MAPs, T waves, etc.) and characteristics thereof (e.g., alternans, activation times, repolarization times, derivatives, etc.).

Cardiac signals are also applied to inputs of an analog-to-digital (ND) data acquisition system 252. The data acquisition system 252 is configured to acquire intracardiac electrogram (IEGM) signals or other action potential signals, convert the raw analog data into a digital signal, and store the digital signals for processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. As is described below, the IEGM signals are used by the ischemia detection module 239 to detect myocardial ischemia.

Various exemplary mechanisms for signal acquisition are described herein that optionally include use of one or more analog-to-digital converter. Various exemplary mechanisms allow for adjustment of one or more parameters associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. Exemplary uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. Impedance measurements for unipolar (electrode to case electrode), bipolar or multipolar electrode configurations may be possible depending on features (e.g., number of leads, switching, number of electrodes, etc). Impedance may be intracardiac, intrathoracic or other.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

First Definition of ST Segment Amplitude Measurement

Figure 3:
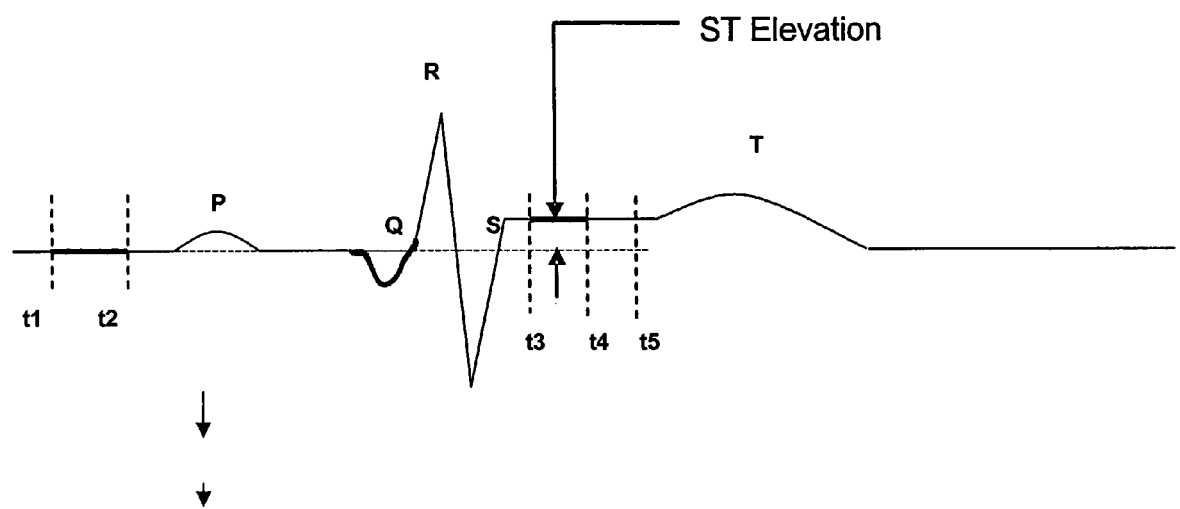
FIG. 3 is a schematic of a typical IEGM signal for a patient suffering from ischemia.

FIG. 3 is a schematic of an IEGM signal for a patient suffering from myocardial ischemia, and shows ST segment elevation resulting from the ischemia. In one illustrative embodiment, the interval between times t3 and t4 defines an early section of the ST segment which will be used to determine ST segment elevation, which the remainder of the ST segment is ignored. In that embodiment, the electrogram amplitude is measured in the interval between times t3 and t4 to monitor for ischemia. In one embodiment, t3 and t4 are preferably selected in such a way that no portion of the T wave will be included. The exemplary values of t3 and t4 are 50 msec and 100 msec after the Q wave, respectively. The window could also be started some amount of time following detection of the R wave (e.g., following the onset of the R wave or following the R wave peak), following the detection of the onset of the QRS complex, or even following the end of the QRS complex.

As shown in FIG. 3, the pre-P wave interval between t1 and t2 is labeled, and in certain embodiments will be used as a reference value in calculating the ST segment elevation. Exemplary values of t1 and t2 are 20 msec and 10 msec before the P wave, respectively. It will also be apparent to those skilled in the art that the reference value may be the period between the P-wave and the QRS complex, or a historical baseline may be used as the reference value.

Effect of Ischemia on ST Segment Amplitude Measurement

Figure 4:
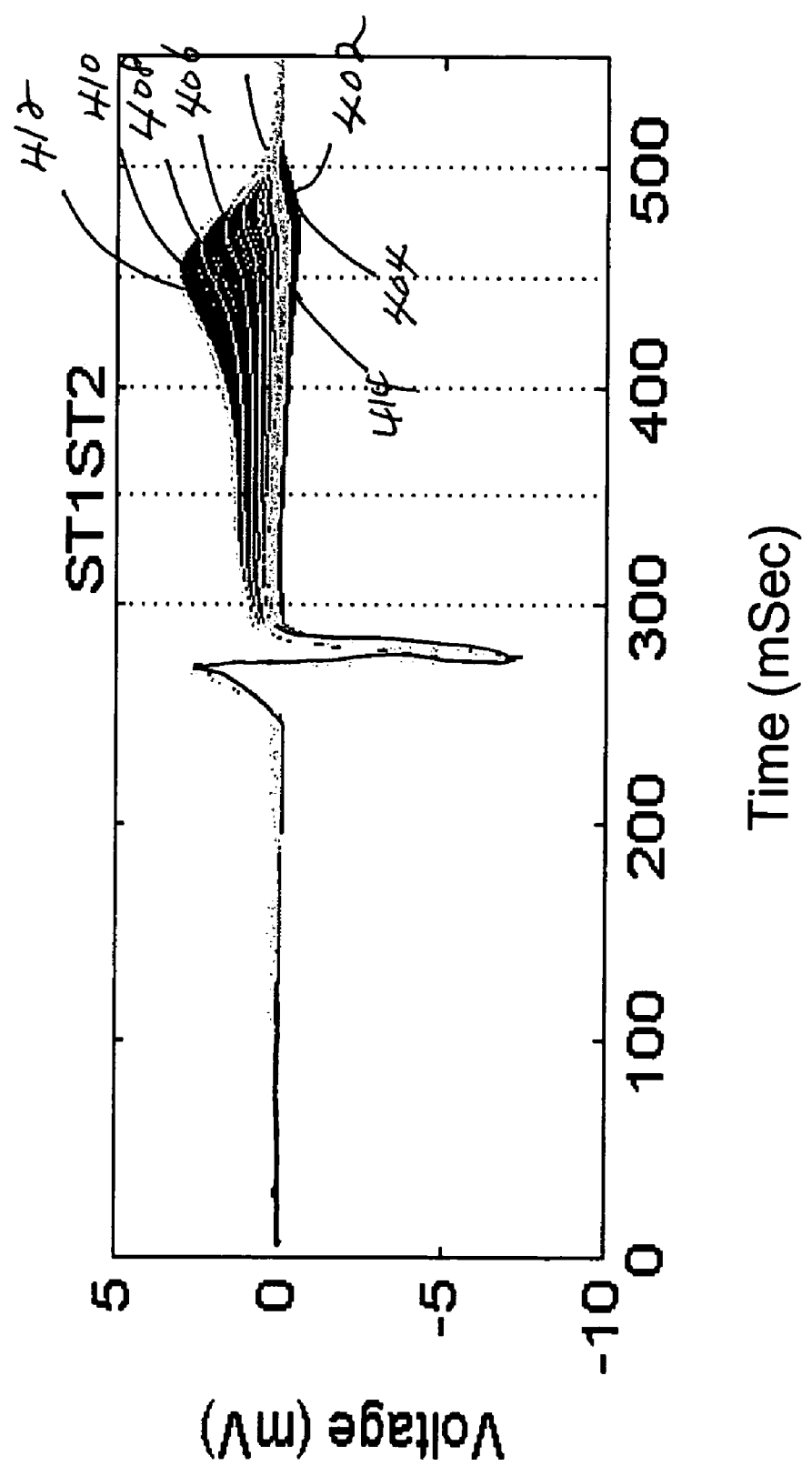
FIG. 4 is a graph illustrating multiple plots showing changes over time as an episode of ischemia progresses.

QRST morphology changes for intrinsic rhythms due to an evolving ischemic condition are shown in FIG. 4. FIG. 4 shows 7 minutes worth of QRST complexes superimposed on each other. The recordings were made from a unipolar right ventricular tip (RVT) electrode in a canine. Bandwidth was 0.05-250 Hz. The ischemic condition was induced by occluding the distal branch of the left anterior descending (LAD) coronary artery. While the recordings were made from a unipolar RVT electrode, it will be apparent to those skilled in the art that many different electrode configurations may be used to make the recordings, including a unipolar right ventricular ring (RVR) configuration, bipolar configurations between the RVT and RVR electrodes, and the like.

As shown in FIG. 4, a first tracing 402 comes from the first minute of non-ischemic baseline condition. At the end of the first minute of recording, the balloon was inflated. A second tracing 404 is from the first minute post occlusion. Third tracing 406 is from 1-2 minutes post occlusion, fourth tracing 408 from 2-3 minutes post occlusion, fifth tracing 410 from 3-4 minutes post occlusion, and sixth tracing 412 from 4-5 minutes post occlusion. Five minutes after the balloon was inflated, it was deflated. A seventh tracing 414 comes from the first minute after deflating the balloon. The changes in ST elevations due to the induced ischemic condition are clearly visible in FIG. 4. The tracings may also be baseline-adjusted by subtracting the pre-P values (discussed earlier) from each sample.

Figure 5:
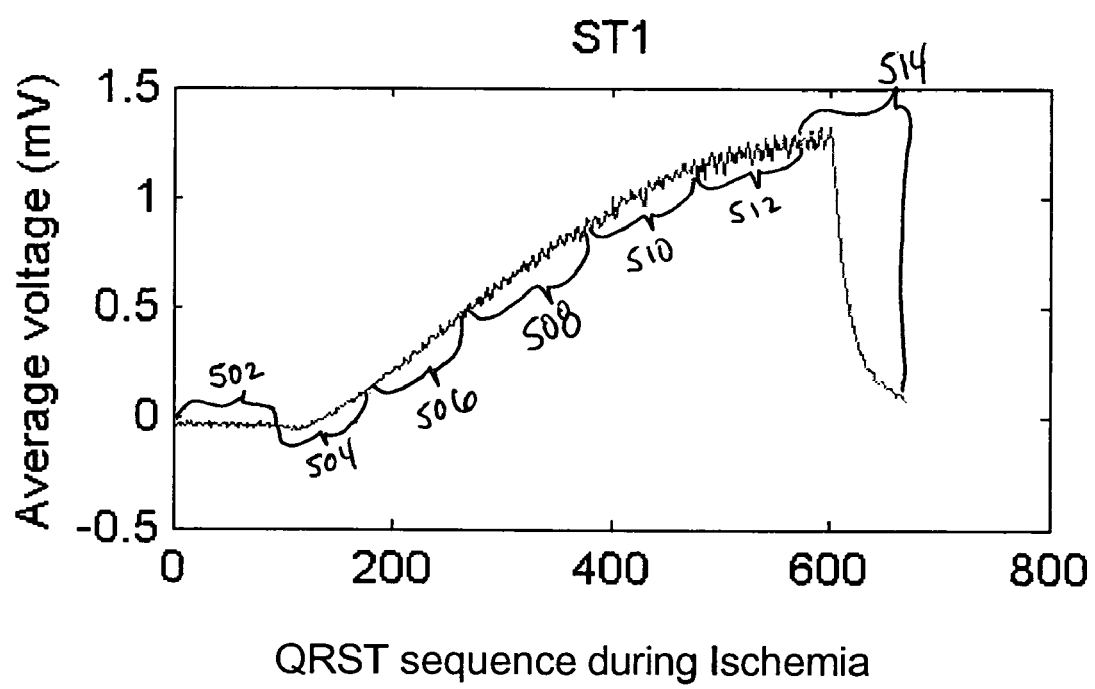
FIG. 5 is a graph tracking ST segment elevation over time for an early portion of the ST segment and ignoring later portions of the ST segment.

The average of EGM amplitude sample values during the period between 50 msec and 100 msec after the Q wave is termed 'ST1'. The time interval over which ST1 is calculated is depicted in FIG. 4 as between 300 and 350 millseconds (i.e., between approximately 50 and 100 milliseconds from the onset of the Q wave). The value of ST1 over the course of an induced ischemic episode (approximately 7 minutes) is shown in FIG. 5. The first region 502 represents non-ischemic baseline EGM level. The second region 504 represents 1 minute into the occlusion. The third region 506 is for 1-2 minute into occlusion, the fourth region 508 for 2-3 minute into occlusion, the fifth region 510 for 3-4 minute into occlusion, the sixth region 512 for 4-5 minute into occlusion and seventh region 514 is after the removal of occlusion by deflating the balloon. ST1 begins to change upon occlusion of the artery (as shown by the second region 504) and the change becomes larger the longer the occlusion remains, reaching the maximum at 5 minutes (sixth region 512). ST1 promptly returns to baseline upon removal of occlusion (seventh region 514).

Figure 6:
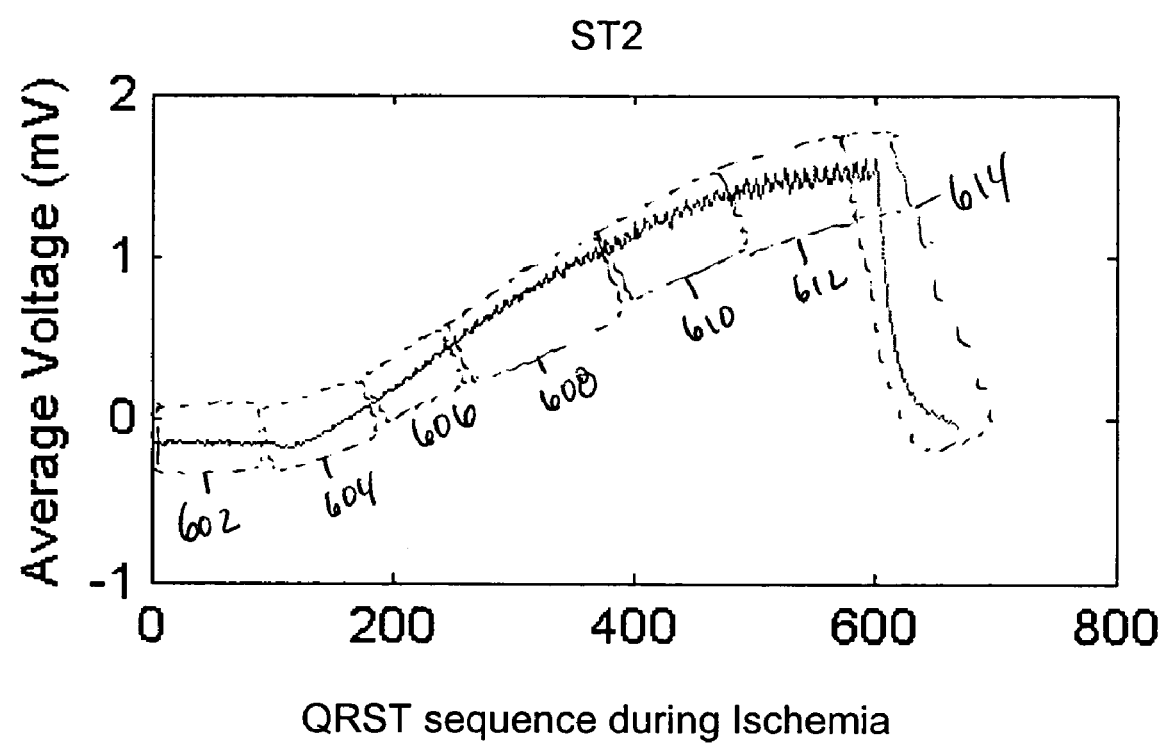
FIG. 6 is a graph similar to that shown in FIG. 5 for another early portion of the ST segment.

A similar trend appears in FIG. 6 which shows the change in average EGM level for the interval between 100 msec and 150 msec after the Q-wave, termed 'ST2' in FIG. 4. These times are also shown as t4 and t5 respectively in FIG. 3. In at least certain embodiments, is not desirable to extend t5 beyond 150 msec after the Q-wave since this may result in the window capturing part of the T wave, as is shown in FIG. 3.

Thus, as shown in FIGS. 5 and 6, the IEGM level change within the early ST segment(s) is a good indication of an ischemic condition. Furthermore, the early ST segment(s) ignore any T-wave signal influences which could adversely affect the measurement.

Figure 7:
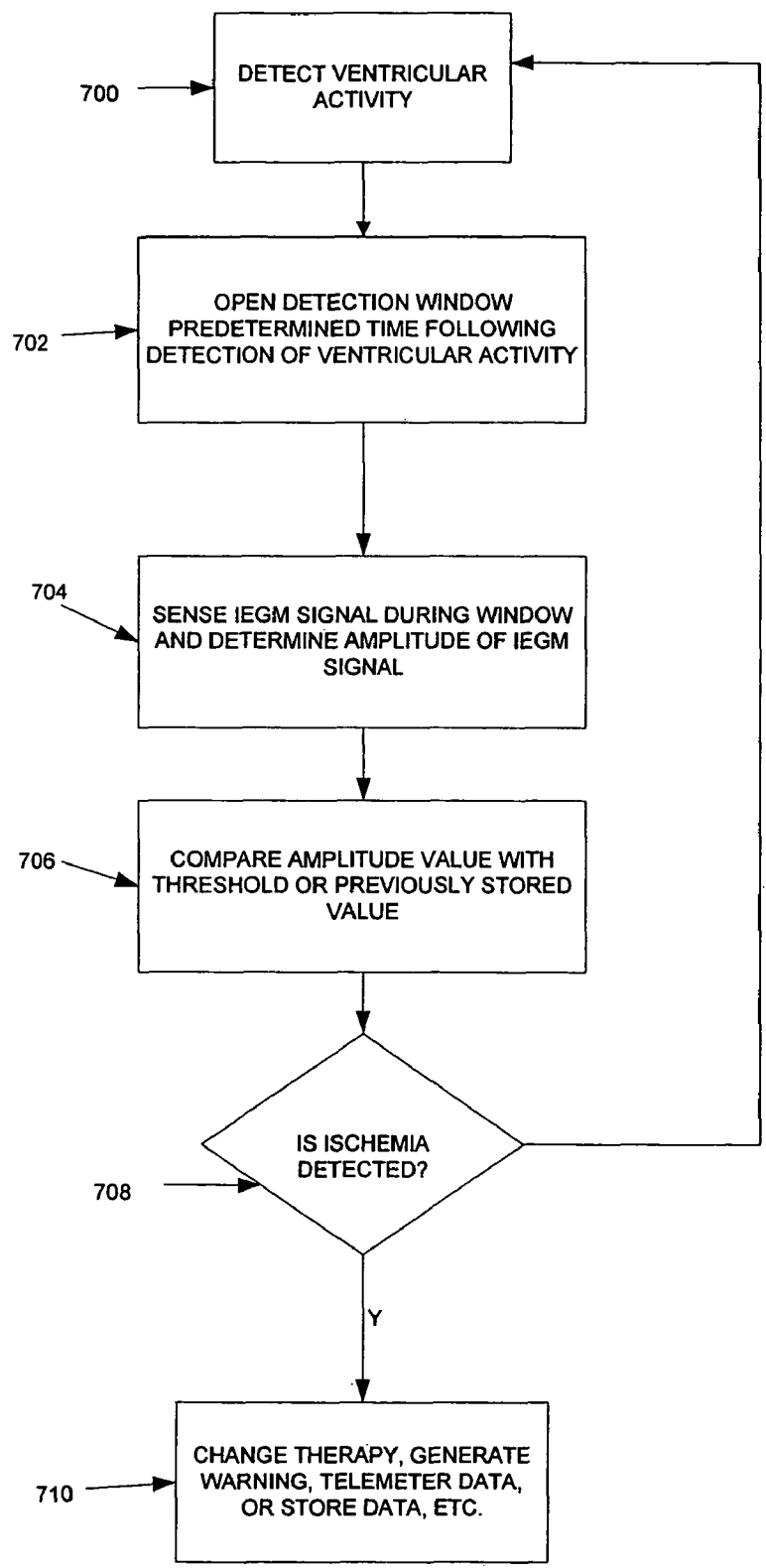
FIG. 7 is a flowchart depicting an illustrative embodiment of a method for detecting ischemia.

Referring now to FIG. 7, one embodiment of a method for detecting ischemia will be described. At step 700, ventricular activity is detected using one or more electrode pairs as described above. At step 702, a detection window is opened for a predetermined time after the ventricular activity is detected. In one embodiment, the window is opened for about 50 milliseconds following the onset of ventricular activity. It will be understood that the window may be opened for a predetermined time following detection of the R-wave peak, or following the end of the QRS complex, or any other suitable event. In addition, the detection window may correspond to the ST1 segment of FIG. 4, the ST2 segment, or any other relatively early portion of the overall ST segment.

At step 704, the portion of the IEGM signal within the window is sensed, and the amplitude of the IEGM signal is determined. As described above, the amplitude may be compared relative to a baseline reference, or to the PQ segment as the reference value. The amplitude may be the maximum value within the window, or an average of the values sensed within the window. Preferably, the pre-P value is determined and used as the reference value to determine the ST segment value within the window. Moreover, as described above, the IEGM signal could be ensemble averaged over a number of cycles, or averaged in some other manner to attenuate noise and other non-cardiac signals.

At step 706, the ST segment value is compared to a threshold or other stored value to determine if the ST segment value indicates myocardial ischemia. In one embodiment, a threshold value is stored in the implanted device 100, and the ST segment value is compared to the threshold value. If the ST segment value exceeds the threshold value, then ischemia is detected at query block 708. In another embodiment, a current ST segment value is compared to a previously stored ST segment value, and if the current value exceeds the previously stored value by more than a predetermined amount, then ischemia is detected.

If ischemia is detected at block 708, operation optionally proceeds to step 710, and some responsive action is preferably taken. For example, the implanted device 100 may change one or more operating parameters in response to detecting ischemia, such as lowering the base pacing rate or otherwise attempting to lower the heart rate (e.g., through neurological stimulation). Alternatively, the implanted device 100 may generate a warning signal to warn the patient of the ischemic condition. The implanted device 100 may also telemeter data and/or a warning to an external device, such as a bedside monitor or other external device. In another embodiment, the implanted device 100 may simply record data corresponding with the detection of ischemia.

General Definition of STn Segment Amplitude Measurement(s)

It will be understood by those skilled in the art that various methodologies may be utilized to determine ST segment values. The following are a few examples of such methodologies.

In one illustrative embodiment, the average ST segment amplitude measurements are made over a plurality of heart cycles. Generally, these measurements will be hereinafter termed STn, where the exemplary cases n=1 and n=2 are defined above. A set of measurements may be made (e.g. STn where n=1 to 5). These measurements may include portions of the IEGM during and/or shortly after onset of the T-wave. This scheme is illustrated in FIG. 4 with five segments separated by vertical dashed lines (only two of which are labeled as ST1 and ST2, the remaining segments would be labeled ST3, ST4, and ST5).

STn Measurement(s) Made on Ensemble Averaged PQRST Complex

To support ischemia detection, in one embodiment the STn values may be measured periodically on an ensemble-average of several (e.g. 8-16) consecutive or closely occurring QRST complexes (e.g., within a few minutes of each other). Ensemble averaging has benefit in that signal components such as noise and respiration artifacts uncorrelated with the cardiac cycle are attenuated. Paced and sensed complexes, if both are occurring, will contribute to separate averaged waveforms. In one embodiment, only sensed complexes are used to determine ST segment values.

STn Measurement(s) Made on Several PQRST Complexes and Statistics Kept

Alternately, the STn values may be measured periodically for each of several individual consecutive or approximately consecutive complexes and statistics calculated on the several measurements. Statistical parameters to be estimated may include the mean and the variance, or any other suitable parameter to determine an average ST segment value for purposes of monitoring for ischemia.

Measurement of Absolute STn Amplitude Vs. Measurement of ΔSTn Amplitude Change Relative to Historical Baseline and Comparison to a Threshold.

ST segment elevation is typically approximately equal to the isoelectric baseline (which in one illustrative embodiment is the pre-P value discussed above) in the absence of a pathological condition. Therefore, STn may be taken as an absolute measurement at any time and ischemia detected if STn exceeds a threshold.

As seen in FIGS. 5 and 6, however, baseline (nonischemic) STn values are not always exactly zero. A nonzero baseline value may arise due to the frequency bandlimiting of asymmetrical QRS complexes. At short AV delays, it may be due to far-field atrial repolarization. It is expected that the baseline may also change slightly over time. It may be affected indirectly by changes in QRS morphology. It may also be affected directly by electrolyte imbalances, such as hypokalemia, which may occur secondary to insulin-induced hypoglycemia. STn changes due to acute ischemia are expected to evolve rapidly (e.g. over the course of a minute or two), where changes due to systemic influences (e.g. hypokalemia) are expected to evolve more slowly.

Therefore, in at least some embodiments it may be desirable to compare STn to one or more historical values on a periodic basis. A change in STn relative to a historical baseline value is hereinafter termed ΔSTn. Ischemia may be detected if ΔSTn exceeds a threshold.

In another embodiment, the implanted device 100 may compute a short-term average value (e.g., taken over a plurality of cycles within the last few minutes) as well as a long-term average value (e.g., taken over a period of weeks, months, etc.). In this embodiment, if a short-term average value exceeds a long-term average value by more than a threshold amount (or alternately by more than a percentage of the long-term average value), then ischemia is indicated. The long-term average value accounts for slowly evolving shifts in the ST segment.

Frequency of STn Measurement and Threshold Comparison

The definition of "historical baseline" above (not to be confused with isoelectric baseline) and the interval at which STn and/or ΔSTn are measured may appropriately depend on the application. For example, for a long-term ischemia burden trend metric, detection might be done relatively infrequently—just frequently enough that it is likely that a detection would occur during an ischemic episode of average length. In this application, STn and/or ΔSTn might be measured every ten minutes with historical baseline values for ΔSTn determined at a single point in time (e.g. at implant or at the command of a clinician) or to the long-term average value determined over a relatively long period of time (e.g. over the previous week).

In the context of acute ischemia event detection, especially where some kind of action might be taken in response, STn and/or ΔSTn might be measured relatively often (e.g. every 30 seconds). In this context, the historical baseline might be more appropriately determined from a relatively recent history (e.g. a moving average of values measured over the previous hour). Acute myocardial ischemia would be indicated in that embodiment if STn and/or ΔSTn measurements exceed corresponding thresholds.

Thus, it will be apparent that the implanted device 100 may store a plurality of thresholds and may monitor for ischemia using a plurality of different detection schemes, some of which being described above.

Criteria for Ischemia Detection

In one embodiment, implanted device 100 might detect ischemia based on a single STn or ΔSTn measurement that exceeds a corresponding threshold. It might be required that several (e.g. 3) consecutive measurements exceed threshold. It might be required that the rate of measurements exceeding threshold exceed a second threshold, e.g. at least 3 of 5 consecutive measurements. Alternately, it might be required that a measure of statistical significance (e.g. T-value) between a set of historical baseline measurements and subsequent set of measurements exceed a threshold.

The T-value is defined as:

$$T\text{value} = (|\text{mean}1 - \text{mean}2|)/\text{sqrt}(std12 + std22)$$

where mean1 and mean2 are the means of the set of historical baseline measurements a set of recent measurements respectively; and std12 and std22 are the variances of the measurements in the historical baseline set and the set of recent measurements, respectively.

$$\text{variance} = \Sigma N(\text{sample}(n) - \text{mean})2/N$$

An exemplary criteria for ischemia detection is Tvalue>2.

Treat Sensed and Paced Complexes Separately

STn and/or ΔSTn measurements may be made on intrinsic or paced complexes, but paced and intrinsic measurements should not be combined and should be evaluated separately. In case of paced complexes, the t3 value (i.e., when the detection window opens) should be greater than t3 in intrinsic complexes since paced complexes tend to have longer QRS durations. Thus, while in one embodiment the t3 value may be 50 milliseconds from detection of the QRS complex for intrinsic complexes, it might be 80 or even 100 milliseconds for paced complexes.

If an intrinsic complex is determined to be the result of a PVC (e.g., through morphology, timing analysis, etc), that complex should not be included in the ST segment measurements.

Adjustment of Measurement for Rate

It may be desirable that the end time (e.g. t4 in FIG. 3) of the segment adapt to heart rate. This is because the QT interval is expected to vary with heart rate, and as described in detail above it is desirable to end the detection window (e.g., ST1, ST2, etc) before the start of the T-wave. This may be accomplished by application of Bazette's equation to estimate the amount of QT shortening at the current rate, and to reduce t4 accordingly.

In another embodiment, if the start and end times of ST1 are correctly chosen, adjustment for rate may not be necessary.

There is an upper limit of rate above which measurements should be considered invalid. This limit is approximately 120 bpm, where the entire ST segment duration is expected to be <70 ms.

Pattern Recognition with Multiple Measurements

It may prove desirable to combine measurements from a set of measurements (e.g. ST1-ST5) in order to improve sensitivity and/or specificity. It may be that such a set of measurements will reveal a pattern unique to ischemia and different from patterns which might be produced by other confounding influences. An example of such a pattern might be an increase in ST1, ST2 and ST3 with ST5 remaining constant or decreasing and with the increase in ST3>increase in ST2>increase in ST1.

For consistency of the above multi-dimensional measurement considering rate variations, it may prove desirable to adjust the duration of all the segments together such that each segment covers a consistent proportion of the overall ST segment as it varies with rate.

It may be that variations in such a pattern might indicate roughly the location of occlusion. Discernment of the existence and location of occlusion may be enhanced by applying these techniques over multiple sensing vectors which may be provided by multiple leads.

Many forms of pattern classifiers which classify multi-dimensional measurements are discussed in the literature may be applicable here. These include classifiers based on Bayesian minimum error, minimum distance and decision trees.

Record of Burden Metric

An implanted device preferably stores a record in memory of the occurrence of ischemic episodes. In one embodiment the ischemic episode data may be processed to define a burden metric, including storing and updating the metric, and displaying it to the user in a useful format.

The burden metric may simply be the ratio of periodic measurements for which ischemia was indicted (X) to the total number of periodic measurements (Y). This may be presented as X of Y or simply Z=X/Y.

The burden metric may include measures of certainty and/or severity of ischemia. This could lead to a multi-dimensional burden metric.

In one embodiment for example, the degree by which a feature exceeds its threshold for ischemia detection may mapped to a severity/likelihood index which can take values from 1-5 where 1 indicates the threshold for detection was barely exceeded and 5 indicates it was exceeded by at least 100%. Then the burden metric above would keep a count of detections of each severity level (e.g. Xn/Y where n=1-5).

If more than one parameter is used for detection, X may be 2-dimensional, e.g. Xn,m where X is a count, n is a severity level and m indicates an enumerated feature. An additional dimension to X may include the value of the activity sensor at the time of measurement.

In the above examples, Y may represent all the measurements made since the last follow-up. Preferably, the metric will be recorded periodically by the device so that changes over time can be observed. Ideally, X would be stored for every measurement. More X/Y would be stored periodically, e.g. every day or every week.

The ischemia burden record is preferably presented to the user as a graph of burden vs. time, analogous to the way atrial tachycardia and atrial fibrillation burden is presented to physicians. Multiple dimensions of X may be presented as separate traces on the graph.

Finally, a measure of correlation between activity sensor output and ischemia burden (or likelihood/severity of ischemia) would be another useful metric. This could be calculated for each point where the ischemia metric is recorded (e.g. daily or weekly), for the entire history in memory, or for both.

Example Embodiments

Figure 8:
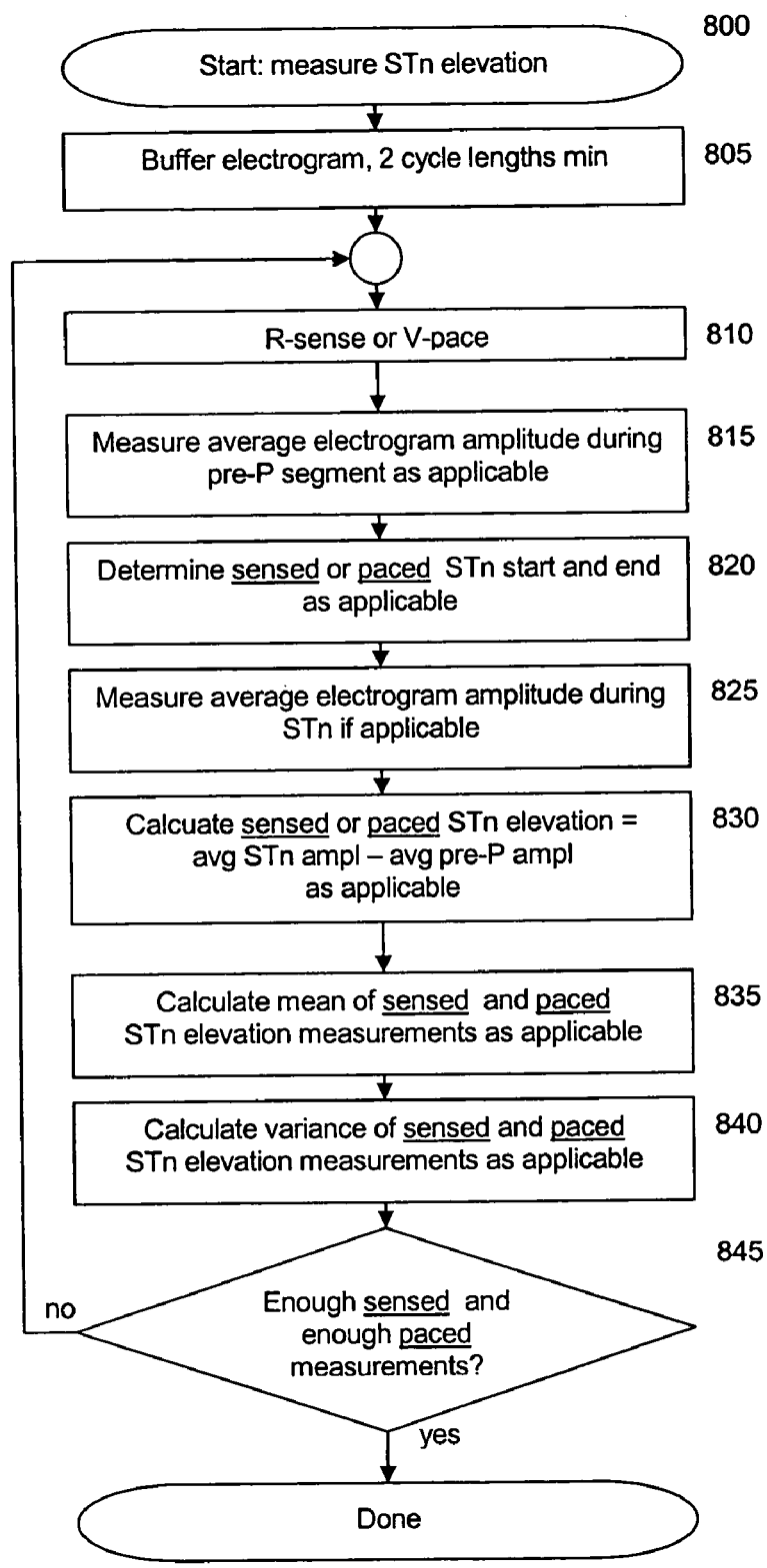
FIG. 8 is a flowchart depicting one illustrative embodiment of a method for making ST segment measurements.

FIG. 8 depicts a process comprising many of the above concepts. When it is time to measure STn, the device begins at 805 to buffer the IEGM for a duration equal to or greater than the time from the end of the previous T-wave to the end of the most recent T-wave, so as to include pre-P isoelectric baseline for the most recent PQRST complex.

Then the process waits at 810 for an appropriate sensed or paced ventricular event. PVCs or events occurring at too high a rate may be excluded as inappropriate.

The following steps are executed on the electrogram signal buffered in memory. In the case where V-pacing is being encouraged or forced (e.g. for ventricular resynchronization therapy,) steps 815-840 may be appropriately skipped for sensed events. In the case where inhibition of ventricular pacing is being encouraged or forced, steps 815-840 may be skipped for paced measurements.

In 815 the pre-P baseline is optionally measured. The t1 and t2 values in FIG. 3 may be determined relative to R-sense or V-pace or relative to P-sense or A-pace. Preferably, the t2 value precedes the start of the P-wave.

In 820, the start and end time(s) of the interval(s) STn are utilized to measure ST segment amplitudes. Because paced QRS complexes are typically longer in duration than intrinsic QRS complexes, start time of STn (e.g. t3 in FIG. 1) may be longer for paced than for sensed complexes. Also because QT depends on rate, the end time of the STn interval (e.g. t4 in FIG. 1) may need to be shortened at higher rates. If measurements are being made for multiple segments, the start and end times of all of them (e.g., ST1, ST2, etc.) may be adjusted.

In step 825 the measurement of average amplitude is made (if applicable) during the applicable interval(s) STn within the ST segment, e.g. between t3 and t4 in FIG. 1.

In step 830, the measurement made in step 825 is preferably referenced to a baseline value by subtracting the pre-P measurement made in step 815. For step 830, it is important to note that if measurements are being made on both paced and sensed complexes, they be stored separately.

Steps 835 and 840 calculate mean and variance respectively for multiple measurements of STn elevation made in multiple passes through steps 815-830. These steps may be done for each pass through steps 815-830 as shown. In one embodiment, moving average techniques may be used to approximate mean and variance. If statistics are not required in step 845, steps 835 and 840 may be carried out once after step 845.

In step 845 it is decided if sufficient paced and sensed measurements have been made. The number of measurements may be a fixed number, e.g. 8 paced events and 8 sensed events. The decision might also involve an evaluation of statistical significance. For example, sufficient paced measurements may have been made if the T value is <2 or if 8 measurements have been made. In the case where V-pacing is being encouraged or forced (e.g. for ventricular resynchronization therapy,) zero sensed events may be enough. In the case where ventricular sensed measurements are preferred (e.g. if ventricular pacing is temporarily being avoided to improve perfusion during an ischemic episode,) zero paced measurements may be enough.

Figure 9:
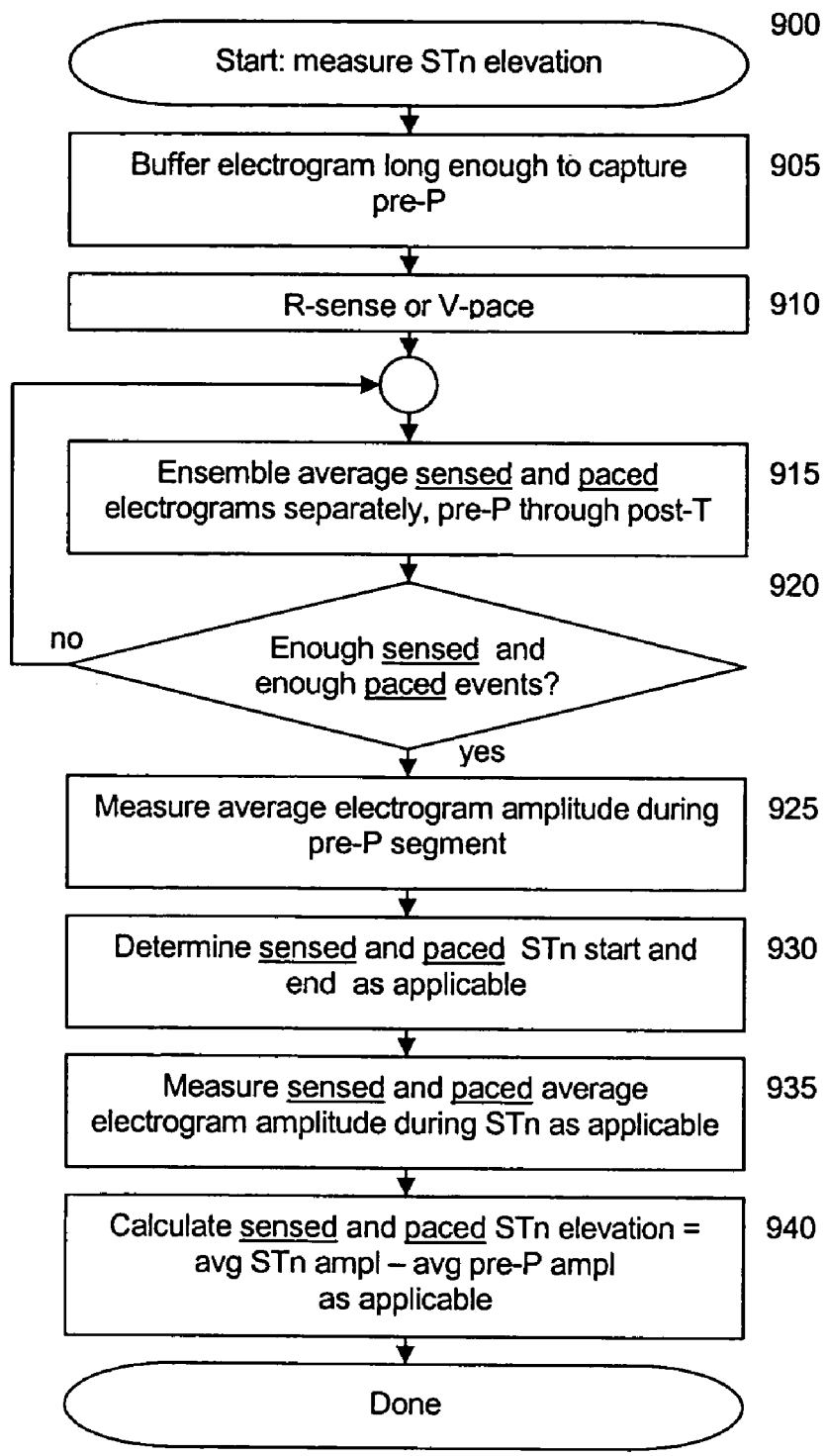
FIG. 9 is a flowchart depicting another illustrative embodiment of a method for making ST segment measurements using ensemble averaging.

FIG. 9 depicts a process which is a variation on the process in FIG. 8.

In step 915, several consecutive or nearly consecutive electrogram complexes are ensemble averaged to produce an averaged pre-P through post-T waveform segment in which non-cardiac signal components such as noise and respiration artifact are attenuated. Paced and sensed complexes, if both are occurring, will contribute to separate averaged waveforms.

Step 920 is analogous to step 845, except that after enough complexes have been averaged, the process proceeds to make a measurement of the electrogram feature(s) of interest. Paced and sensed averaged complexes are handled independently.

Steps 925-940 are analogous to steps 815-830.

Figure 10:
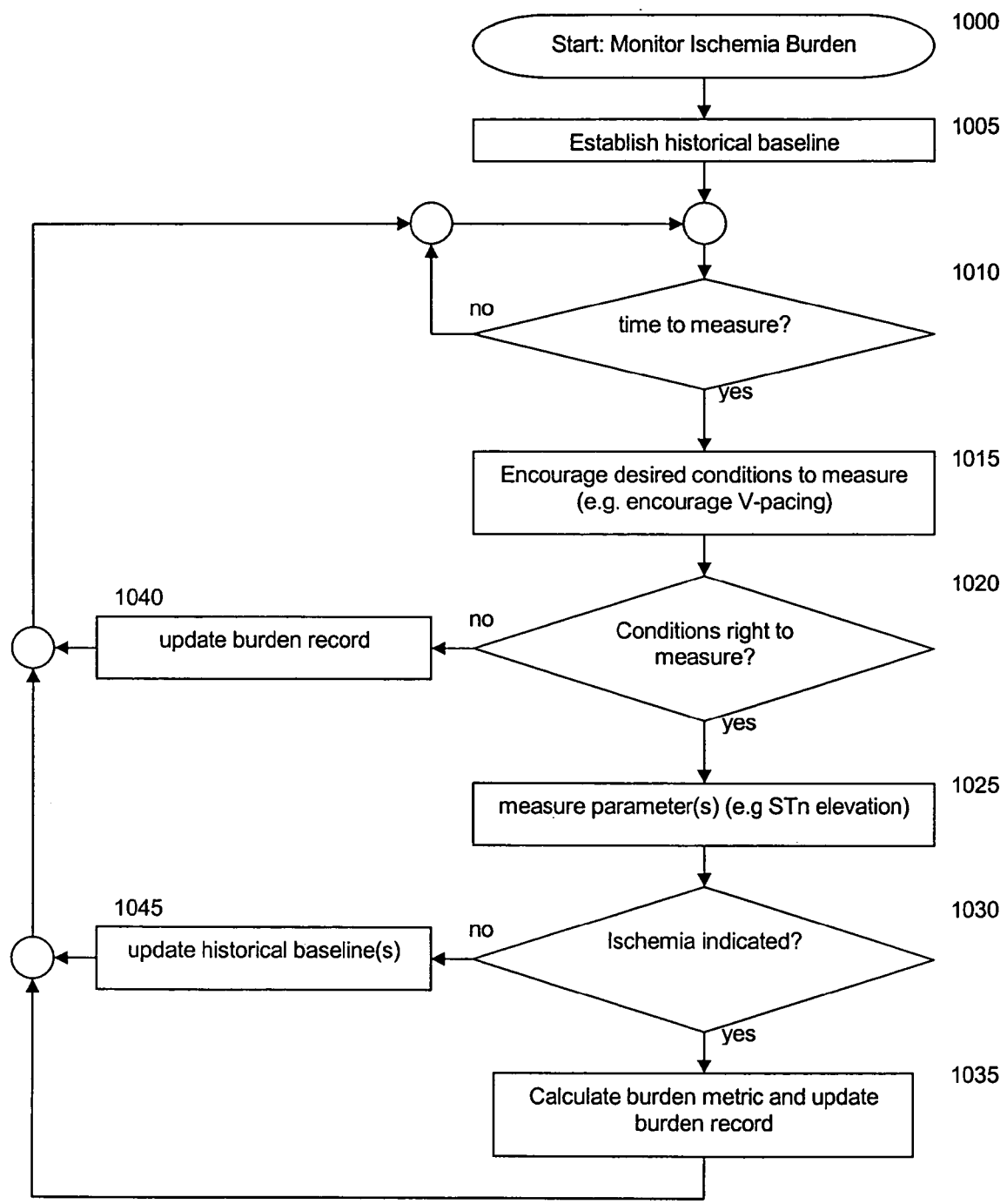
FIG. 10 is a flowchart depicting another illustrative embodiment of a method for detecting ischemia.

FIG. 10 shows one illustrative embodiment of a method for monitoring ischemia burden.

At step 1005, an initial historical baseline is preferably established. This would occur at some predetermined time (e.g., at implant) or per a command from a programmer. This step is not needed if only absolute feature measurements are to be made. Historical baseline information may be stored in the fomi(s) discussed above, e.g. in the form of feature measurement mean(s) and optionally variance(s).

At step 1010, the process waits until it is time to make a measurement. Appropriate measurement intervals for ischemia burden monitoring range from every 30 seconds to every day. An interval in the range from 1-10 minutes is preferred. Instead of or in addition to a regular interval for measurements, measurements may be set to occur at specific times of day and/or when the patient has been at rest (as indicated by an activity sensor) for a predetermined time.

At step 1015, pacing therapy is optionally adjusted to provide favorable conditions for measurement. For example, AV hysteresis may be envoked to encourage V-pacing or inhibition if primarily paced or sensed measurements are desired. In a ventricular resynchronization therapy device, V-V timing may be adjusted. The pacing rate may be slowed to a target rate if it is currently elevated, e.g. due to rate response for activity. The pacing rate may be slightly increased to a target rate temporarily to provoke ischemia in case myocardial oxygen demand is on the verge of exceeding supply.

Step 1020 optionally confirms that favorable conditions for measurement exist. If they do not, e.g. if the intrinsic rate is too fast, a measurement is not made at this time. Rather the existence of unfavorable conditions is optionally logged at step 1040, and the process returns to step 1010. The time to the next measurement may be optionally advanced.

At step 1024, the parameter(s) of interest is/are measured, e.g. STn according to the processes in FIG. 8 or FIG. 9. It should be noted that any number of parameters for ischemia detection may be used here. These include, among others, QT max, QT end, QRS morphology, PR segment amplitude.

At step 1030, it is determined whether or not the measurement indicates ischemia is present. This determination may be made per any of the methods discussed above, e.g. comparing the absolute measurement(s) to a threshold, comparing the recent measurement to a historical baseline, or evaluating a pattern classifier for multiple parameters. Any of these methods may also involve evaluation of statistical significance, as discussed above.

If ischemia is not indicated at step 1030, historical baselines are optionally updated at step 1045. As discussed above, historical baseline information may be updated by keeping one or more moving averages of parameter mean(s) and variance(s). For example, a fast average (e.g. over the last hour), a slow average (e.g. over the last day or longer) or both may be updated.

If ischemia is detected at step 1030, a burden metric is preferably calculated and the record of burden is updated as discussed above. In addition, the implanted device 100 may take appropriate action, such as generating a warning signal, telemetering out data to an external device, and the like.

What is claimed is:

1. A method of detecting and treating ischemia comprising:
sensing ventricular activity with an implantable medical device;
opening a window a predetermined time after sensing the ventricular activity, wherein the window is shorter than an ST segment;
determining an amplitude value within the window;
processing the amplitude value to detect ischemia;
wherein determining an amplitude value comprises measuring the amplitude value relative to an isoelectric baseline; and
if ischemia is detected, automatically changing one or more cardiac pacing parameters with the implantable medical device.

2. The method of claim 1 wherein the window is between 50 and 100 milliseconds after the onset of a Q wave.

3. The method of claim 1 wherein the window is between 100 and 150 milliseconds after the onset of a Q wave.

4. The method of claim 1 wherein the isoelectric baseline is measured during an interval between a T-wave and subsequent P-wave.

5. The method of claim 1 wherein processing the amplitude value comprises comparing the amplitude value to a threshold.

6. The method of claim 5 wherein the threshold is an historical baseline value.

7. The method of claim 5 wherein the threshold is a long-term average value.

8. The method of claim 1 wherein opening a window comprises opening the window at a first time if the ventricular activity is intrinsic, and at a second time if the ventricular activity is paced.

9. The method of claim 1 and further comprising computing an ischemia burden value based on the processing and detecting of ischemia.

10. The method of claim 1 wherein changing one or more cardiac pacing parameters comprises lowering base pacing rate.

11. A system for detecting and treating ischemia comprising:
means for sensing ventricular activity with an implantable medical device;
means for opening a window a predetermined time after sensing the ventricular activity, wherein the window is shorter than an ST segment;
means for determining an amplitude value within the window;
means for processing the amplitude value to detect ischemia;
wherein the means for determining an amplitude value within the window comprises means for measuring the amplitude value relative to an isoelectric baseline; and
if ischemia is detected, means for automatically changing one or more cardiac pacing parameters with the implantable medical device.

12. The system of claim 11 wherein the means for opening a window comprises means for opening the window between 50 and 100 milliseconds after the onset of a Q wave.

13. The system of claim 11 wherein the means for opening a window comprises means for opening the window between 100 and 150 milliseconds after the onset of a Q wave.

14. The system of claim 11 wherein the means for processing the amplitude value comprises means for comparing the amplitude value to a threshold.

15. The system of claim 11 wherein the isoelectric baseline is measured during an interval between a T-wave and subsequent P-wave.

16. The system of claim 11 wherein means for changing one or more cardiac pacing parameters comprises lowering base pacing rate.

* * * * *